(12) United States Patent
Deli et al.

(10) Patent No.: US 8,075,578 B2
(45) Date of Patent: Dec. 13, 2011

(54) APPARATUS AND METHOD FOR MAKING A CIRCULAR INCISION

(75) Inventors: Josef Deli, Carmiel (IL); Erez Levy, Yishuvei Gederot (IL)

(73) Assignee: V.R. Hexis Ltd., Tel Aviv (IL)

( * ) Notice: Subject to any disclaimer, the term of this patent is extended or adjusted under 35 U.S.C. 154(b) by 326 days.

(21) Appl. No.: 12/408,841

(22) Filed: Mar. 23, 2009

(65) Prior Publication Data

US 2010/0241130 A1   Sep. 23, 2010

(51) Int. Cl.
*A61B 17/32* (2006.01)
(52) U.S. Cl. .................................. 606/166; 606/180
(58) Field of Classification Search .................. 606/107, 606/166–168, 170–172, 178–180
See application file for complete search history.

(56) References Cited

U.S. PATENT DOCUMENTS

| | | |
|---|---|---|
| 4,708,138 A | 11/1987 | Pazandak |
| 4,911,161 A | 3/1990 | Schechter |
| 5,261,923 A | 11/1993 | Soares |
| 5,269,787 A | 12/1993 | Cozean, Jr. et al. |
| 5,423,841 A | 6/1995 | Kornefeld |
| 5,464,417 A | 11/1995 | Eick |
| 5,522,829 A | 6/1996 | Michalos |
| 5,728,117 A | 3/1998 | Lash |
| 5,860,994 A | 1/1999 | Yaacobi |
| 5,873,883 A | 2/1999 | Cozean, Jr. et al. |
| 6,165,190 A | 12/2000 | Nguyen |
| 6,629,980 B1 | 10/2003 | Eibschitz-Tsimhoni |

OTHER PUBLICATIONS

International Search Report for International Application No. PCT/IL10/00225 mailed on Jul. 9, 2010.

*Primary Examiner* — Ryan Severson
(74) *Attorney, Agent, or Firm* — Pearl Cohen Zedek Latzer, LLP (57) ABSTRACT

An apparatus is described for making a circular incision in a surface. The apparatus includes a handle and an elongated blade assembly extending from the handle. The blade assembly includes a rotor. The rotor includes a bar having an elongated axis, with at least one blade extending from the bar. The rotor is adapted to rotate about an axis substantially parallel to the blade, the blade being substantially perpendicular to the elongated axis of the bar. The blade assembly is adapted to extend the blade for making the circular incision and to retract the blade. In the retracted state, the bar is aligned with the blade assembly, preventing direct contact between the blade and the surface.

15 Claims, 6 Drawing Sheets

APPARATUS AND METHOD FOR MAKING A CIRCULAR INCISION

FIELD OF THE INVENTION

The present invention relates to surgical instruments. More particularly, the present invention relates to an apparatus and method for making a circular incision.

BACKGROUND OF THE INVENTION

Cataracts may be caused by clouding of the crystalline lens of the eye. The accepted treatment for cataracts includes cataract surgery. During cataract surgery, the affected lens is removed and may be replaced with an artificial lens.

In order to perform cataract surgery, a small incision is made in the cornea of the eye. In order to facilitate healing and avoid unnecessary damage to the eye, the incision should be made as small as possible. An instrument (or instruments) is inserted through the incision. The instrument is used to make a small opening in the anterior capsule of the lens, a membranous structure that contains the lens. This procedure is referred to as capsulorhexis. The instrument reaches the anterior capsule via the pupil. Once the opening in the anterior capsule is made, the nucleus of the affected lens may be broken into smaller pieces and removed through the opening. An artificial replacement lens may then be inserted. The replacement lens may be supported by the posterior capsule and by the structure that supports the capsule.

The opening in the anterior capsule is often made using an instrument resembling a bent needle that is inserted into the eye through the incision in the cornea. The bend in the instrument enables insertion of the point of the instrument through the pupil to the anterior capsule while avoiding the iris. The surgeon manipulates the point of the instrument, perhaps with the assistance of forceps or other instruments, so as to make a generally circular opening in the anterior capsule. An exceptionally high degree of skill may be required in order to make such an opening without tearing or jagged edges, and without causing damage to other structures associated with the lens. Tears or jagged edges may lead to uncontrolled tearing of the anterior capsule, of the posterior capsule (possibly causing exposure of the vitreous humor), or otherwise complicate the surgery and the healing process that follows.

Devices have been described previously for assisting the surgeon in performing capsulorhexis. Shechter in U.S. Pat. No. 4,911,161 describes a cutting apparatus similar to the bent needle used in traditional capsulorhexis, but provided with a mechanism for vibrating the needle. Kornefeld in U.S. Pat. No. 5,423,841 describes an intraocular knife with a controller on the handle for changing the angle of the blade during the course of cutting the anterior capsule. Such a knife may be difficult to insert through a small incision in the cornea, and may be difficult to manipulate properly during capsulorhexis. Both of these devices require the surgeon to manipulate the instrument so as to make the desired circular opening in the anterior capsule.

Other devices have been described for making a circular opening in the manner of a "cookie cutter." Cozean, Jr. et al. in U.S. Pat. No. 5,269,787 describe a capsulorhexis apparatus with a circular cutting edge. An ultrasonic power source vibrates the cutting edge, causing it to cut a circular hole in the anterior capsule. In U.S. Pat. No. 5,873,883, Cozean, Jr. et al. describe a similarly shaped apparatus, where the circular opening is made by forcing an incompressible fluid on the anterior capsule through an annular orifice. In order to insert either of these devices into the eye, a sufficiently large incision in the cornea must be made. Such an incision may be significantly larger than an incision made during standard capsulorhexis.

Lash in U.S. Pat. No. 5,728,117 describes a capsulorhexis instrument that is designed to overcome the requirement for a large incision in the cornea. The cutting edge of the instrument may be deformed and retracted into a narrow tube for insertion through a small incision. Once inserted, the instrument is extended out of the tube where it resumes its original circular shape. The surgeon then applies pressure on the instrument, causing the cutting edge to press against and cut a circular opening in the anterior capsule. Eibschitz-Tsimhoni in U.S. Pat. No. 6,629,980 also describes an instrument that may be inserted through a small corneal incision. The described instrument has a dual-edged semicircular blade. The surgeon presses the blade onto the anterior capsule to make a semicircular cut. The blade is then turned over to make a second, reversed semicircular cut adjacent to the first, together forming a circular opening. Use of both of these instruments requires the surgeon to manually apply a regulated but relatively large amount of force to the instrument. An error made in applying such a force may result in damage to structures in the eye.

Finally, Yaacobi (U.S. Pat. No. 5,860,994) and Nguyen (U.S. Pat. No. 6,165,190) describe instruments that move a knife in a circular path in order to make a circular opening. The shapes of these instruments, with the knife extending outward from the main shaft of the instrument, may make it difficult to insert the instrument through a small incision.

Therefore, there is a need for an instrument capable of simple and safe insertion through a small incision in an outer layer, and of making a circular incision in an inner layer, while reducing the force needed to be exerted by the surgeon when using the instrument.

It is an object of the present invention to provide an apparatus and method for assisting a surgeon in making a circular incision.

Other aims and advantages of the present invention will become apparent after reading the present invention and reviewing the accompanying drawings.

SUMMARY OF THE INVENTION

There is thus provided, in accordance with some embodiments of the present invention, an apparatus for making a circular incision in a surface. The apparatus includes a handle and an elongated blade assembly extending from the handle. The blade assembly includes a rotor comprising a bar having an elongated axis, with at least one blade extending from the bar, the rotor being adapted to rotate about an axis substantially parallel to the blade, and the blade being substantially perpendicular to the elongated axis of the bar. The blade assembly is adapted to extend the blade for making the circular incision, and to retract the blade. In the retracted state, the bar is aligned with the blade assembly, preventing direct contact between the blade and the surface.

Furthermore, in accordance with some embodiments of the present invention, the apparatus includes a drive mechanism for operating the rotor.

Furthermore, in accordance with some embodiments of the present invention, the drive mechanism is manual.

Furthermore, in accordance with some embodiments of the present invention, the drive mechanism includes a wire for rotating a shaft of the rotor.

Furthermore, in accordance with some embodiments of the present invention, the drive mechanism includes an operating knob coupled to the wire for causing the rotor to rotate.

Furthermore, in accordance with some embodiments of the present invention, the operating knob is confirmed to a slot in the handle.

Furthermore, in accordance with some embodiments of the present invention, the drive mechanism includes an elastic element coupled to the wire for causing the rotor to rotate.

Furthermore, in accordance with some embodiments of the present invention, the rotor is adapted to extend from the blade assembly when rotated in one direction and is adapted to retract back to the blade assembly when rotated in the opposite direction.

Furthermore, in accordance with some embodiments of the present invention, the rotor includes a projecting shaft which is provided with threading and which is inserted in a socket with corresponding threading.

Furthermore, in accordance with some embodiments of the present invention, the rotor is adapted to extend a distance substantially equal to 0.25 mm when rotated in one direction through an angle of 360°.

Furthermore, in accordance with some embodiments of the present invention, the handle and the blade assembly are joined so as to define an obtuse angle.

Furthermore, in accordance with some embodiments of the present invention, the blade assembly includes at least one protective projection for preventing direct contact between said at least one blade and the surface when the bar is in the retracted state.

Furthermore, in accordance with some embodiments of the present invention, the apparatus includes two blades.

Furthermore, in accordance with some embodiments of the present invention, a cutting edge of the blade is convex.

There is further provided, in accordance with some embodiments of the present invention, a minimally invasive method for making a circular incision in a tissue surface covered by a tissue layer. The method includes providing an apparatus for making a circular incision in the surface. The provided apparatus includes a handle, and an elongated blade assembly extending from the handle. The blade assembly includes a rotor comprising a bar having an elongated axis, with at least one blade extending from the bar, the rotor adapted to rotate about an axis substantially parallel to the blade, the blade being substantially perpendicular to the elongated axis of the bar. The blade assembly is adapted to extend the blade for making the circular incision, and retract the blade. In the retracted state the bar is aligned with the blade assembly, avoiding direct contact between the blade and the surface. The method further includes inserting the blade assembly in the retracted state through an incision in the tissue layer. The method further includes placing the blade assembly in a desired position over the tissue surface and operating the blade assembly to make the circular incision.

Furthermore, in accordance with some embodiments of the present invention, the tissue surface is an anterior capsule of an eye.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF EMBODIMENTS

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

An instrument for cutting a circular incision, in accordance with embodiments of the present invention, includes an assembly of one or more cutting blades. The blade assembly is mounted at the end of a handle. Alternatively, the blade assembly may be integral to the handle. The handle may be held by a surgeon, or other user (or perhaps an arm of a surgical robot) near one end, which is designated the proximal end. The opposite, distal, end of the instrument holds the blade assembly. The blade assembly is thin and narrow so as to pass unimpeded through a small incision in an outer layer of tissue. In general, the blade assembly may extend from the handle so as to form an obtuse angle with the handle. A cutting side of the blade assembly may be placed on, or in contact with, a tissue surface in which a circular incision is to be made. Each cutting blade is mounted on a rotor. In order to minimize the profile of the rotor for insertion through and incision, the rotor may be in the form of an elongated bar. The rotor includes a shaft, which projects from the blade assembly. Each cutting blade is mounted such that its cutting edge is oriented substantially perpendicular to the rotation plane and to the long axis of the rotor (i.e. parallel to the shaft), and parallel to the direction of rotation. The cutting edge faces outward from the blade assembly on the cutting side, toward a surface with which the assembly may be in contact. Rotation of the rotor thus moves each cutting blades parallel to its cutting edge. Thus, when the cutting edge is in contact with a surface, rotating the shaft and the rotor coupled to the shaft causes the cutting edge to cut a circular incision in the surface. The cutting edge is shaped and sharpened such that the cutting edge need merely be drawn across the surface in order to cut it. For example, the cutting edge may have a convex, curved shape. It may not be necessary to apply pressure or force to the blade assembly in order to cut.

For example, when placed in contact with the anterior capsule of the eye, the cutting edges of the blade assembly may be made to perform capsulorhexis.

The shaft of the rotor may be provided with pitched threading and a socket in the blade assembly into which the shaft is inserted may be tapped with similar threading. When the shaft rotates in one direction, the pitched threading causes the shaft to extend out of the socket, extending the cutting blades outward from the blade assembly. Extending the cutting blades outward exposes the cutting edges of the blades. When the shaft rotates in the opposite direction, the shaft and blades are retracted inward. The blade assembly may include a housing with protective projections. When the blades are completely retracted, the cutting blades are shielded from contact with an adjacent surface by the protective projections of the housing.

The shaft may be rotated by means of a transmission mechanism. The transmission mechanism allows a drive mechanism located on the handle to rotate the shaft. By locating the drive mechanism on the handle, the size of the blade assembly may be minimized. For example, the transmission mechanism may include a string or wire that is looped around, and inserted into, a gear mechanism, a hydraulic or pneumatic system. The drive mechanism may include mechanical means, such as a movable handle, spring, or coil, an electric motor, or any other suitable drive mechanism.

In some embodiments of the present invention, the transmission mechanism may include a wire that is moved by a drive mechanism with mechanical elements. A middle portion of the wire is wrapped around the shaft and passes through bored openings in the shaft. The handle of the instrument includes conduit grooves and hollow passageways through which the wire passes. One end of the wire is connected to a sliding element in the form of a cylinder that may be slid within a hollow section of the handle. An operating knob extends radially outward from the cylinder. The knob fits within an elongated slot on the handle, the slot being oriented along the length of the handle. The knob may be moved a limited distance within the slot. Sliding the knob backward, toward the proximal end of the handle, pulls the attached end of the wire backward. Pulling on the attached end of the wire causes the portion of the wire that is looped around and through the shaft to rotate the shaft. Rotating the shaft causes the rotor and the cutting edges of the cutting blades to rotate and extend outward from the blade housing. When the blade housing is placed against a suitable surface, the rotation and extension of the blades makes a circular incision in the surface. In embodiments of the present invention, sliding the knob backward the entire length of the slot may rotate the rotor through about 360°. The other end of the wire is attached to a second sliding element that is free to travel inside a second hollow portion of the handle. The other, proximal end of the second sliding element is attached to the free end of an elastic element or spring. The other end of the spring is fixed. Thus, when the knob is used to pull on one end of the wire, extending the cutting blades from the housing, the spring is stretched.

Once the knob is pulled fully back, the knob may be released. Releasing the knob then releases the tension on the end of the wire attached to the cylinder sliding element. Releasing the tension on the wire releases the tension on the spring. The spring may then relax, pulling the end of the wire that is attached to the second sliding element in the opposite direction. Pulling the wire in the opposite direction rotates the shaft in the opposite direction. When rotating in the opposite direction, the rotor and cutting blades are retracted into the housing. When the spring has fully relaxed, the cutting blades are fully shielded by the housing. At this point the surgeon may remove the blade assembly of the instrument via the incision.

Reference is now made to the Figures.

Figure 1:
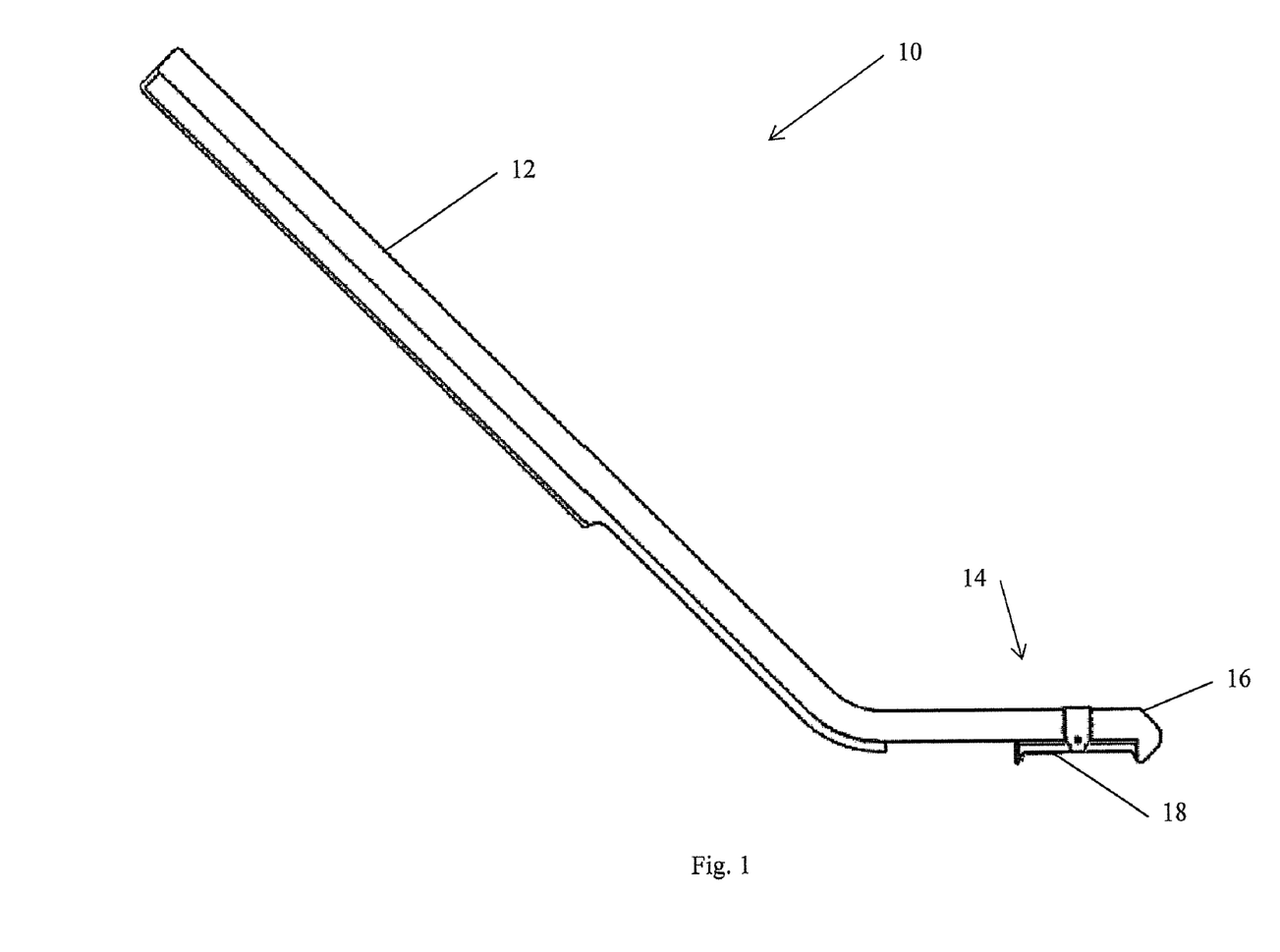
FIG. 1 is a side view of an instrument for making a circular incision, in accordance with embodiments of the present invention.

FIG. 1 is a side view of an instrument for making a circular incision, in accordance with embodiments of the present invention. Circular incision instrument 10 includes a handle 12 and blade assembly 14. Blade assembly 14 includes blade housing 16. Components of handle 12 and blade assembly 14 may be constructed of bio-compatible, durable and heat tolerant plastic or polymer, or any other material suitable for the construction of handles and components of medical instruments. Handle 12 and blade assembly 14 are oriented with respect to one another so as to form an obtuse angle.

Figure 2:
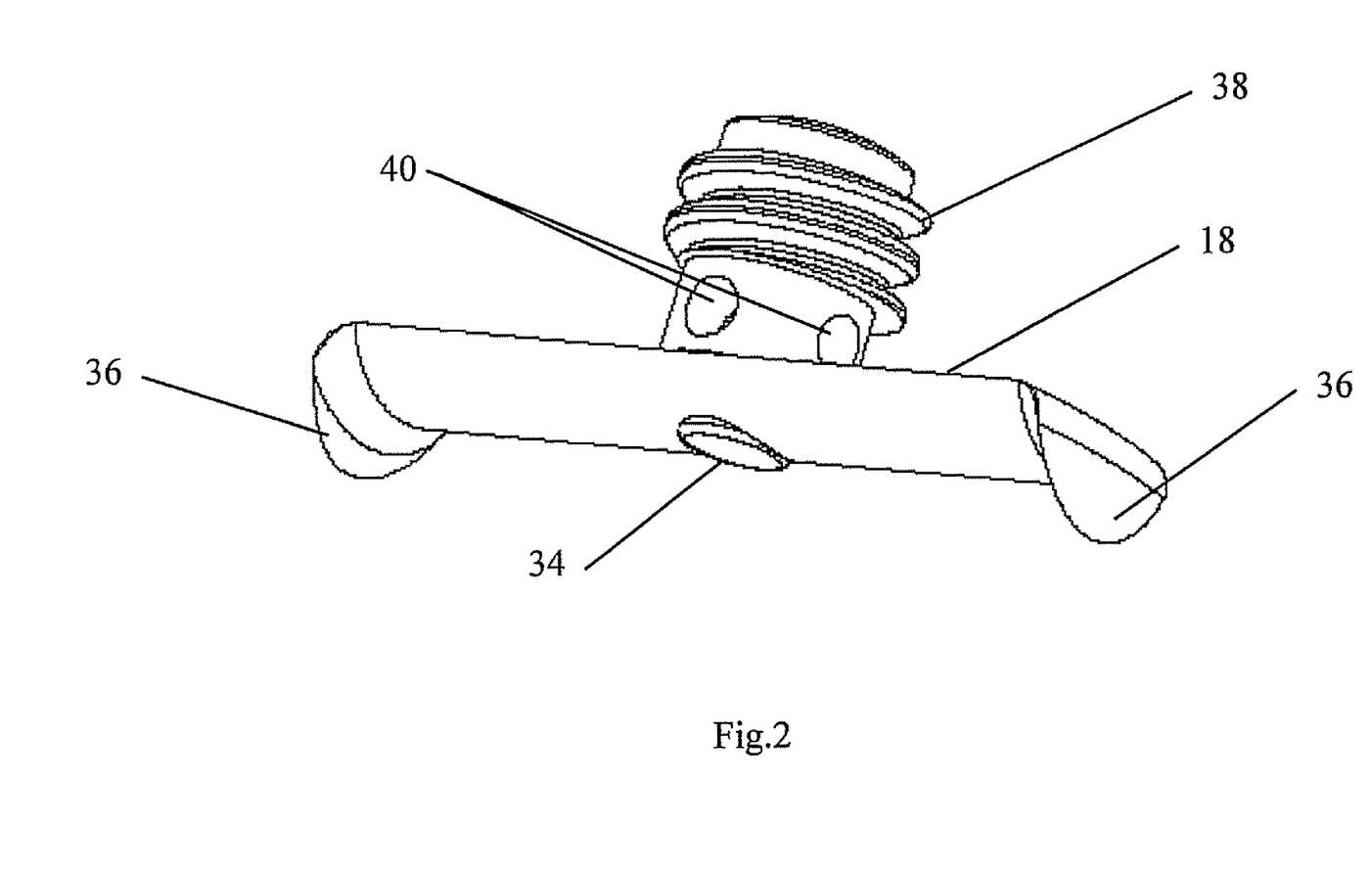
FIG. 2 shows the rotor of the instrument shown in FIG. 1.

FIG. 2 shows the rotor of the instrument shown in FIG. 1. Rotor 18 is coupled to shaft 34. In order to prevent relative motion between rotor 18 and shaft 34, rotor 18 may be welded, or otherwise firmly attached, to shaft 34. Alternatively, shaft 34 and rotor 18 may be formed as an integral single piece. Shaft 34 is provided with pitched threading 38. Two cutting blades 36 are mounted on the ends of rotor 18. Cutting blades 36 may be made, for example, of stainless steel. The cutting edge of each cutting blade 36 is designed to cut tissue when the blade is drawn across the tissue surface in a direction parallel to the cutting edge. The cutting edge is designed to cut the tissue with minimal force applied toward moving the cutting edge across the tissue surface. In order that the cutting edge cut the tissue, little or no force needs be applied either perpendicular or parallel to the surface. Shaft 34 may be rotated by means of application of tension to an end of a wire looped around shaft 34 and through bores 40.

Figure 3:
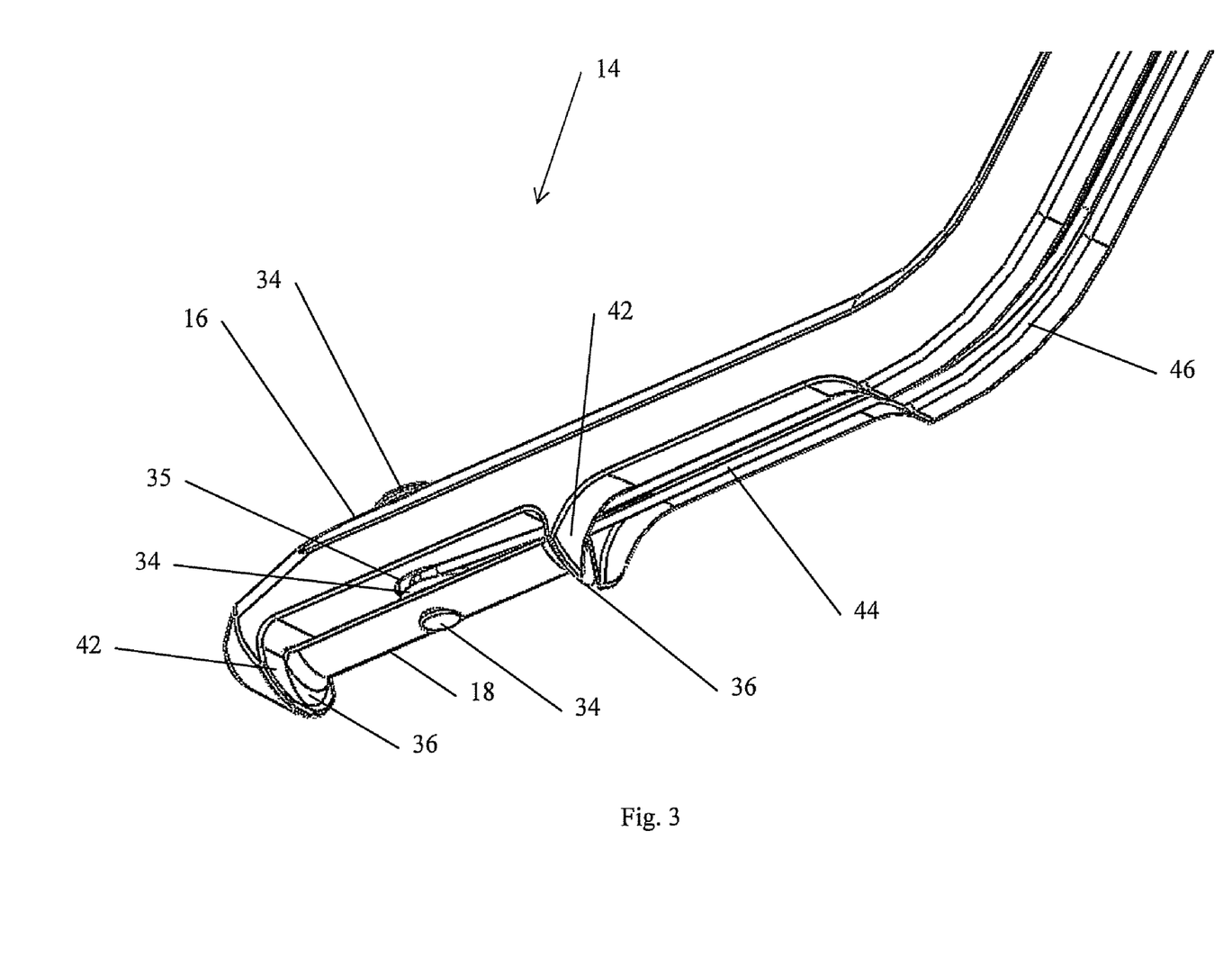
FIG. 3 shows part of the rotor rotation mechanism of the instrument shown in FIG. 1.

FIG. 3 shows part of the rotor rotation mechanism of the instrument shown in FIG. 1. One part of wire 44 connected to one end of wire 44 wraps around shaft 34 before passing through bores 40 (FIG. 2). Pulling on that end of wire 44 of which part is wrapped around shaft 34 unwraps that part of the wire from shaft 34. Unwrapping the part of wire 44 causes shaft 34 to rotate, while wrapping part of the other end of wire 44 about shaft 34. Wrapping part of the other end about shaft 34 enables rotation of shaft 34 in the opposite direction by means of pulling on that other end of wire 44. The ends of wire 44 extend through channel 46 to attachment points within handle 12 (FIG. 1).

FIG. 3 shows rotor 18 in a retracted state. In the retracted state, cutting blades 36 are retracted such as not to extend beyond protective projections 42 of blade housing 16. In the retracted state, cutting blades 36 may not contact or cut a surface or object against which blade assembly 14 is placed. Wire 44 is looped around shaft 34 and through bores 40 (FIG. 2). For example, wire 44 may be looped 270° around shaft 34. When one end of wire 44 is pulled, shaft 34 is rotated in one direction. For example, pulling one end of wire 44 causes a clockwise rotation of shaft 34. Clockwise rotation is here defined as clockwise when shaft 34 is viewed from the end of shaft 34 that is inserted into socket 35, looking outward toward rotor 18. Clockwise rotation of shaft 34 causes pitched threading 38 (FIG. 2) on shaft 34 to unthread from the matching threading in socket 35. Thus, shaft 34 is extended outward from socket 35. Extending shaft 34 outward extends rotor 18 outward. Outward extension rotor 18 extends the cutting edges of cutting blades 36 to beyond protective projections 42 of blade housing 16, exposing the cutting edges. As rotor 18 continues to rotate and to extend outward, the cutting edges continue to extend, enabling the cutting edges to cut deeper into a surface. The distance through which rotor 18 extends during a given rotation of rotor 18 depends on the pitch of pitched threading 38. The distance may be adapted to the intended use of the instrument. For example, in an instrument designed to perform capsulorhexis, the pitched threading on shaft 34 may be designed to extend the cutting edges outward by about 0.25 mm during a clockwise rotation through about 360°.

Pulling on the other end of wire 44, after shaft 34 is extended, causes a counterclockwise rotation of shaft 34, retracting shaft 34 into socket 35. Retracting shaft 34 retracts the cutting edges of cutting blades 36 to within protective projections 42. In the above example, rotating shaft 34 counterclockwise through about 360° may cause complete retraction of cutting blades 36 to within blade housing 156.

Figure 4:
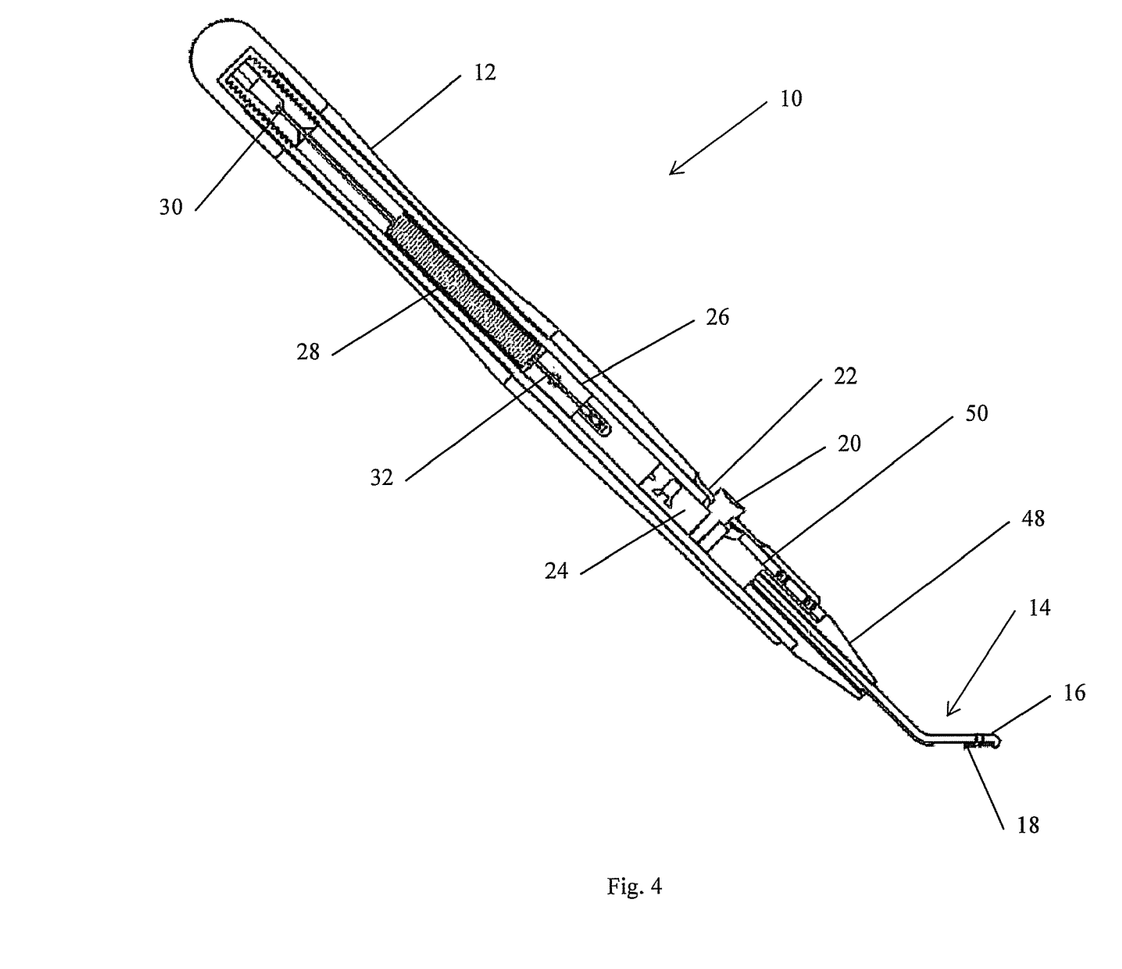
FIG. 4 shows interior mechanisms of the instrument shown in FIG. 1.

FIG. 4 shows interior mechanisms of the instrument shown in FIG. 1. The ends of wire 44 (FIG. 3) extend from blade assembly 44 into handle 12 through hollow channels in conic tube 48 and tube 50. One end of wire 44 is attached to cylinder 24. For example, cylinder 24 may be constructed out of two semi-cylindrical pieces with the attached end of wire 44 held between the pieces. Firmly attaching the pieces to one another, such as by means of one or more screws, may hold the end of the wire firmly between the pieces. Knob 20 is attached to cylinder 24. Knob 20 may be slid back and forth within slot 22. Sliding knob 20 backward away from blade assembly 14 pulls the end of wire 44 that is attached to cylinder 24.

The other end of wire 44 is attached to sliding element 26. Also attached to sliding element 26 is free end 32 of spring 28. Fixed end 30 of spring 28 is fixed within handle 12.

When knob 20 is pulled backward within slot 22, the end of wire 44 that is attached to cylinder 24 is also pulled backward. Pulling backward on the attached end of wire 44 causes rotor 18 to rotate in a clockwise direction (as defined above). As rotor 18 rotates clockwise, rotor 18 and the attached cutting blades are extended. When knob 20 reaches the back end of slot 22, rotor 18 will have rotated through a predetermined angle, for example 360°. Rotor 18 and the attached cutting blades will have extended out of blade housing 16 by a predetermined amount. Concurrently, the other end of wire 44 pulls on attached sliding element 26. Pulling on sliding element 26 applies tension to free end 32 of spring 28, stretching spring 28.

At this point, knob 20 may be released. Releasing knob 20 releases the tension applied to spring 28 via wire 44. Spring 28 may then relax, pulling on sliding element 26 and the attached end of wire 44. Pulling on the end of wire 44 attached to sliding element 26 causes rotor 18 to rotate in a counterclockwise direction (as defined above). Counterclockwise rotation of rotor 18 causes rotor 18 and the attached cutting blades to retract into blade housing 16. The other end of wire 44 pulls on attached cylinder 24, pulling cylinder 24 forward toward blade assembly 14. Forward movement of cylinder 24 pulls attached knob 20 forward within slot 22.

Figure 5A:
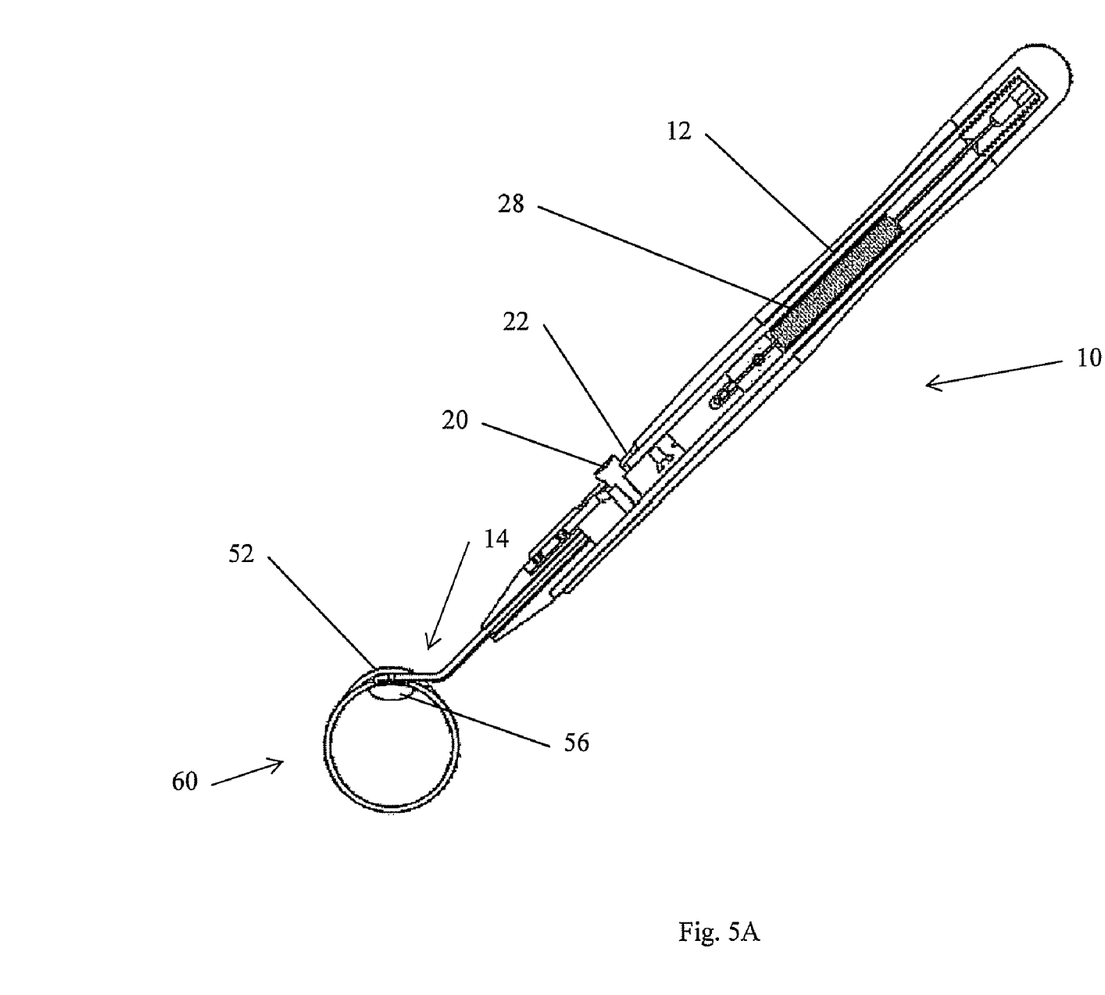
FIG. 5A illustrates performance of capsulorhexis with an instrument in accordance with embodiments of the present invention.
Figure 5B:
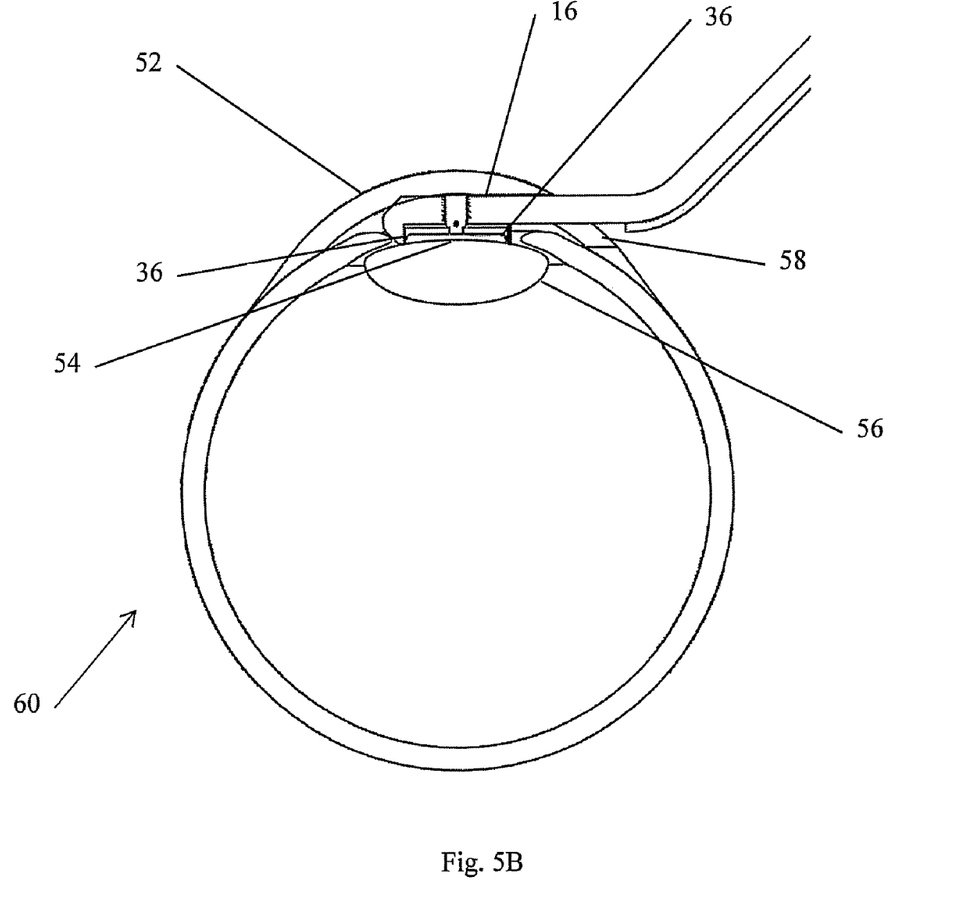
FIG. 5B is an enlargement of a portion of FIG. 5A.

A method for making a circular incision with an instrument in accordance with an embodiment of the present invention is now described. The method may be used to perform any surgical procedure requiring a circular incision, in particular when the incision is made on the surface of a layer of tissue underlying an outer layer. However, the present discussion will discuss the method in connection with capsulorhexis. FIG. 5A illustrates performance of capsulorhexis with an instrument in accordance with embodiments of the present invention. FIG. 5B is an enlargement of a portion of FIG. 5A. First, a small incision 58 is made in cornea 52 of eye 60. The size of incision 58 may be sufficiently large to allow insertion of blade assembly 14 of instrument 10 and any other required instruments, but no larger. Handle 12 of instrument 10 may then be held with the fingers of one hand. The end of blade assembly 14 distal to handle 12 may then be inserted through incision 58. In order to facilitate insertion, the profile of blade assembly 14 in the direction perpendicular to incision 58 may be minimized by rotating blade assembly 14 by about 90° relative to the orientation shown in FIG. 5 (such that instrument 10 would lie horizontally in the Figure). Once the portion of blade assembly 14 including blade housing 16 is inserted, instrument 10 is rotated to the orientation shown in FIG. 5. Handle 12 remains outside of incision 58.

The bottom of blade assembly 14 is placed in contact with anterior capsule 54 of lens 56. No pressure need by applied. Knob 20 is then pulled backward, in a direction away from blade assembly 14. For example, knob 20 may be pulled backward using one finger of the hand holding handle 12. Knob 20 is pulled until it reaches the back end of slot 22. Pulling knob 20 backward rotates and extends cutting blades 36. As cutting blades 36 rotate through a clockwise (as defined above) angle of about 360° and extend outward, a circular incision is cut in anterior capsule 54. Knob 20 may then be released. Release of knob 20 allows spring 28 to rotate cutting blades 36 counterclockwise and retract them. When cutting blades 36 are retracted, blade assembly 14 may then be removed through incision 58, rotating instrument 10 as needed.

Thus, embodiments of the present invention provide an apparatus and method for inserting a blade assembly through a small incision in an outer layer and making a circular incision in an inner layer.

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the present invention.

The invention claimed is:

1. An apparatus for making a circular incision in a surface, the apparatus comprising:
   a handle;
   an elongated blade assembly extending from the handle, the blade assembly including a rotor comprising a bar having an elongated axis adapted to rotate about a rotation axis substantially perpendicular to the elongated axis of the bar, and two blades having, each, a curved cutting edge, the blades substantially perpendicular to and extending from the bar opposite each other on either sides of the axis of rotation; and
   a drive mechanism for rotating the rotor to make a circular incision in the surface and for aligning the bar with an end portion of the handle adjacent to the rotor when desired.

2. The apparatus of claim 1, wherein the rotor is adapted to extend the blades to make the circular incision and to retract the blades, wherein in the retracted state the bar is aligned with the end portion of the handle adjacent to the rotor, preventing direct contact between the blades and the surface.

3. The apparatus of claim 2, wherein the rotor is adapted to extend from the end portion of the blade when rotated in one direction and is adapted to retract back towards the end portion of the handle adjacent to the rotor when rotated in the opposite direction.

4. The apparatus of claim 3, wherein the rotor includes a projecting shaft which is provided with threading and which is inserted in a socket with corresponding threading.

5. The apparatus of claim 3, wherein the rotor is adapted to extend a distance up to 0.25 mm when rotated in said one direction through an angle of 360°.

6. The apparatus of claim 4, wherein the end portion of the handle adjacent to the rotor includes at least one protective projection for preventing direct contact between the blades and the surface when the bar is in the retracted state.

7. The apparatus of claim 1, wherein the drive mechanism is manual.

8. The apparatus of claim 7, wherein the drive mechanism includes a wire for rotating a shaft of the rotor.

9. The apparatus of claim 8, wherein the drive mechanism includes an operating knob coupled to the wire for causing the rotor to rotate.

10. The apparatus of claim 9, wherein the operating knob is confined to a slot in the handle.

11. The apparatus of claim 8, wherein the drive mechanism includes an elastic element coupled to the wire for causing the rotor to rotate.

12. The apparatus of claim 1, wherein the end portion of the handle adjacent to the rotor and the rest of the handle define an obtuse angle.

13. The apparatus of claim 1, wherein the curved cutting edge is convex.

14. A minimally invasive method for making a circular incision in a tissue surface covered by a tissue layer, the method comprising:

providing an apparatus for making a circular incision in the surface, the apparatus comprising a handle, an elongated blade assembly extending from the handle, the blade assembly including a rotor comprising a bar having an elongated axis adapted to rotate about a rotation axis substantially perpendicular to the bar, and two blades having, each, a curved cutting edge, wherein the blades are substantially perpendicular to and extending from the bar opposite each other on either sides of the axis of rotation, and a drive mechanism for rotating the rotor to make a circular incision in the surface and for aligning the bar with an end portion of the handle adjacent to the rotor when so desired;

inserting the blade assembly with the rotor aligned with an end portion of the handle which is adjacent to the rotor through an incision in the tissue layer; and placing the blade assembly in a desired position over the tissue surface and operating the blade assembly to make the circular incision.

15. A method as claimed in claim 14, wherein the tissue surface is an anterior capsule of an eye.

* * * * *